United States Patent [19]
Dobkin

[11] Patent Number: 5,735,821
[45] Date of Patent: Apr. 7, 1998

[54] SURGICAL ATTACHMENT DEVICE

[76] Inventor: William R. Dobkin, 6020 Lido La., Long Beach, Calif. 90803

[21] Appl. No.: 546,783

[22] Filed: Oct. 23, 1995

Related U.S. Application Data

[63] Continuation of Ser. No. 369,010, Jan. 5, 1995, abandoned.

[51] Int. Cl.$^6$ ............................................. A61M 5/32
[52] U.S. Cl. ............................................. 604/174; 604/180
[58] Field of Search ............................................. 604/174, 177, 604/170, 179, 180

[56] References Cited

U.S. PATENT DOCUMENTS

| | | | |
|---|---|---|---|
| 4,435,174 | 3/1984 | Redmond et al. | 604/174 |
| 4,632,670 | 12/1986 | Mueller, Jr. | 604/174 |
| 5,354,282 | 10/1994 | Bierman | 604/180 |

*Primary Examiner*—Michael Powell Buiz
*Assistant Examiner*—N. Kent Gring
*Attorney, Agent, or Firm*—Kenneth W. Float

[57] ABSTRACT

Apparatus for securing one or more suction tubes, hoses, electrical and/or endoscopic cables, and intravenous and cardiovascular bypass tubing during an operation. The apparatus is a surgical attachment device that comprises a member (preferably molded plastic) having at least one opening adjacent a first surface thereof. A first portion of each opening is designed to slidably secure the tubes, hoses or cables. A second portion of each opening immediately adjacent the first surface is smaller than the dimension of the first portion. The first portion of each opening tapers from a narrow dimension at the center of the member to a wide dimension at opposite ends of the member. Each opening has a plurality of inwardly projecting tapered ribs disposed around its internal periphery that taper from their narrowest dimension at the center of the opening to their widest dimension at the ends of each opening. The inwardmost edges of the plurality of tapered ribs have a dimension nominally equal to or narrower than the narrowest dimension of the tapered opening. The tapered ribs assist in securing the tubes, hoses or cables in the opening and prevent unwanted sliding thereof. The inwardmost edges of the ribs contact the tubes, hoses or cables when they is inserted into the opening. One pair of ribs or projections are larger than the others and are initially encountered when a hose or tube is pressed into the first portion of the opening. This configuration secures the various hoses and tubes, and the like, within the second portion of the opening and prevents their inadvertent pullout. An adhesive layer is disposed on a second external surface of the member for securing it to a surgical drape during an operation. The surgical attachment device may be flexible or deformable between the first and second portions of each opening to permit passage of nonflexible tubes, hoses or cables through the second portion of the opening. This may be achieved by adding additional lower slots separated from selected openings by hinge areas that provide for easy flexing of the member at the openings to permit insertion of the tubes, hose, or cables therein. The flexible portion comprises one or more living hinge areas that flex to open each of the openings.

23 Claims, 4 Drawing Sheets

SURGICAL ATTACHMENT DEVICE

CROSS REFERENCE TO RELATED APPLICATIONS

This application is a continuation of U.S. patent application Ser. No. 08/369,010, filed Jan. 5, 1995, now abandoned.

BACKGROUND

The present invention relates generally to medical equipment, and more particularly, to a surgical attachment device that is used to secure tubes, wires, hoses, electrical cables, video cables and fiber optic cables during an operation.

During surgical operations, it is customary for surgeons and other operating room personnel to employ suction tubes to remove blood, tissue and other cellular debris from a patient that is undergoing an operation, and air-driven pneumatic tools that are driven by an air source(s) coupled to the tools by way of pneumatic hoses. Furthermore, it is customary to use electrosurgical instruments that are used as cutting and coagulation tools during surgery. These electrosurgical instruments are connected to electrical equipment by way of electrical cables. Unipolar electrosurgical instruments transmit current through the patient to a grounding pad, while bipolar electrosurgical instruments transmit current between the two heads of bipolar forceps. The electrosurgical instruments, pneumatic tools, and cables are used in almost all surgeries. More recently, endoscopic surgery has proliferated. These surgeries require fiber optic light cables and video camera cables passing to and from the operative field, respectively.

During surgery, it is common practice to store the electrosurgical instruments and tools in a self-adherent plastic pocket of a drape that is disposed over the patient when they are not in use. This also provides easy access for the surgeon. The cables and hoses that connect the electrosurgical instruments and tools to their electrical equipment, air sources and endoscopic equipment are loosely gathered together adjacent an extremity of the patient and are secured by wrapping a portion of the drape around the cables and then holding them in place using a surgical clamp. In a similar fashion, the suction tubes are also routed and clamped in place, typically by the same type of surgical clamp. As should be clear from this typical operating room scenario, the cables are not very well controlled and in many instances interfere with the operation, or may become dislodged or contaminated.

Accordingly, and in order to overcome the limitations of conventional operating room practices, it is an objective of the present invention to provide for a surgical attachment device that is used to secure tubes, wires, hoses, electrical cables, video cables and fiber optic cables during an operation.

SUMMARY OF THE INVENTION

In order to meet the above and other objectives, the present invention is a surgical attachment device for securing one or more cylindrically shaped members, including tubes and/or cables, such as suction tubes, hoses, electrical cables, video cables and fiber optic cables during an operation. The surgical attachment device comprises a member, that is preferably comprised of molded plastic, having at least one opening or groove formed therein adjacent a first surface thereof. A first portion of each opening is designed to slidably secure a particular cylindrically shaped member, such as a suction tube, hose, or unipolar, bipolar, or endoscopic cable, for example. A second portion of each opening immediately adjacent the first surface is dimensioned to be slightly smaller than the dimension of the first portion of the opening. The first portion of each opening tapers from a narrow dimension adjacent the center of the member to a wide dimension adjacent opposite ends of the member.

Each opening has a plurality of inwardly projecting tapered ribs disposed around its internal periphery that taper from their narrowest dimension adjacent the center of the opening to their widest dimension at the ends of each opening. The inwardmost edges of the plurality of tapered ribs have a dimension substantially equal to or narrower than the narrowest dimension of the tapered opening. The plurality of tapered ribs assist in securing the cylindrically shaped member in the opening and prevent unwanted sliding thereof. The inwardmost edges of the ribs contact the cylindrically shaped member when it is inserted into the opening. A first set of ribs, or projections, disposed adjacent the interface between the first and second portions of the opening are larger than the others and prevent inadvertent pull-out of the various tubes, hoses, wires and cables from the opening.

An adhesive layer is disposed on a second external surface of the member so that it may be secured to a surgical drape during an operation. The adhesive layer may be affixed or otherwise coated onto the second surface of the member and a backing layer may be disposed thereon. The backing layer covers the adhesive layer prior to use, and is removed to expose the adhesive layer and secure the surgical attachment device to the drape.

The surgical attachment device may comprise a member that is flexible or deformable between the first and second portions of each opening to permit passage of noncompressible or fragile cylindrically shaped members through the second portion of the opening into the first portion thereof. This may be achieved by modifying the surgical attachment device to include additional lower slots separated from selected openings by hinge areas that provide for easy flexing of the member at the openings to permit insertion of the tubes, hose, or cables therein. The flexible portion of the member comprises one or more living hinge areas that flex to open each opening.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
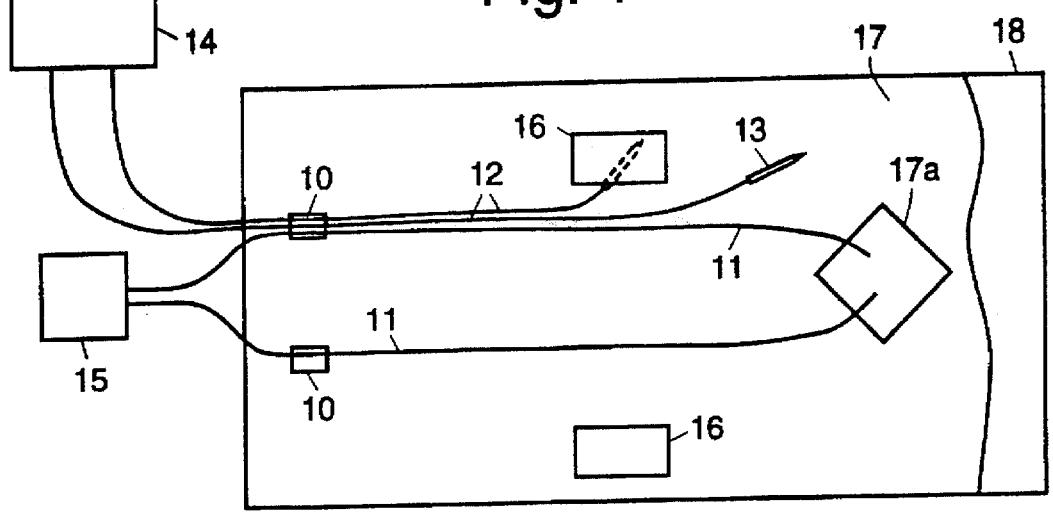
FIG. 1 shows a typical operating room scenario employing surgical attachment devices in accordance with the principles of the present invention.

Referring to the drawing figures, FIG. 1 shows a typical operating room scenario employing surgical attachment devices 10 in accordance with the principles of the present invention. FIG. 1 shows an operating room table 18 on which is disposed a surgical drape 17 the is used to cover a patient (not shown) during an operation. The drape has an opening 17a therein that exposes an area of the patient that is to be operated on. Self-adhering plastic pockets 16 are attached to the drape 17 in which surgical instruments 13 may be stored when not in use. Typical surgical instruments 13 include electrosurgical instruments 13 used for cutting and coagulation of tissues, endoscopic instruments 13 used for minimally invasive surgery in various body cavities, or pneumatic air-driven instruments 13 of all types, intravenous lines and cardiovascular bypass tubes 11. Flexible intravenous (I–V) tubes 11 are run from I–V solution bags 14b to the patient. A fiber optic light source cable and video cable 12 may be coupled between a light source and video camera 14c and optical instruments 13 that are used to illuminate and view the operative field, for example.

The surgical instruments 13 are connected to electrical equipment 14 (controller 14) in a conventional manner by means of unipolar and bipolar electrical cables 12 for the cauterizing instruments 13, endoscopic cables 12 for the endoscopic instruments 13, and hoses 12a for pneumatic air-driven instruments 13. In addition, suction tubes 11 are coupled to a vacuum pump 15 and are used to remove blood, tissue and other cellular debris from the patient during the operation. Intravenous tubes 11 passes to the patient and cardiovascular bypass tubes 11 pass to and from a cardiovascular bypass pump 14a. A compressed air pump 15a may be coupled to a compressed air tube 11.

Figure 2:
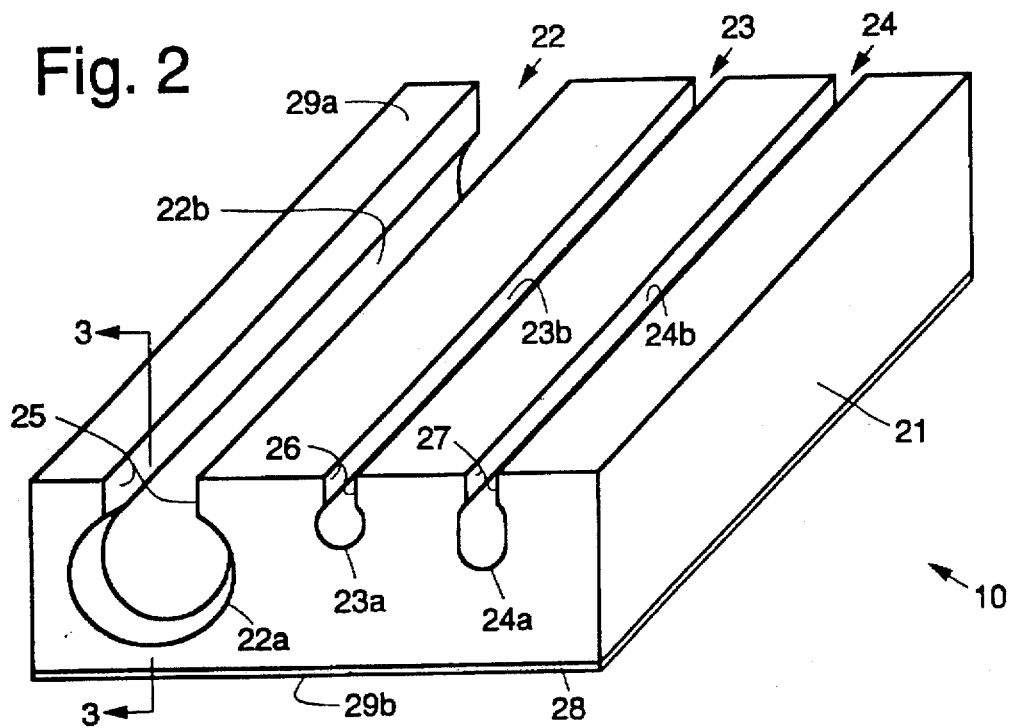
FIG. 2 is an end view of a first embodiment of the surgical attachment device in accordance with the present invention.
Figure 3:
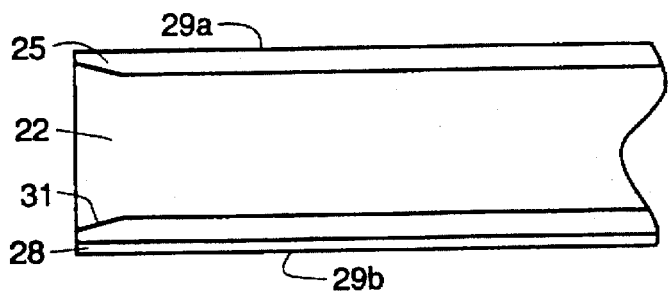
FIG. 3 is a cross sectional top view of the surgical attachment device of FIG. 2 taken along the lines 3—3.

The surgical attachment devices 10 of the present invention is used to secure the respective suction tubes 11 and electrical or endoscopic cables 12, and the like, in an orderly manner during the operation. FIG. 2 is an end view of a first embodiment of the surgical attachment device 10a in accordance with the present invention. FIG. 3 is a cross sectional top view of the surgical attachment device 10a of FIG. 2 taken along the lines 3—3.

The first embodiment of the surgical attachment device 10a is comprised of a member 21 that may be a block of plastic, such as polyethylene or polystyrene, for example. The member 21 is a single piece structure that has an outer body 23 with a plurality of inwardly extending supporting ribs 24 that mate with an opening 22, or groove 22. The opening 22 or groove 22 is formed adjacent a first surface 29a of the member 21. The opening 22 may have flared ends 29.

The opening 22 has a first portion 22a that typically has a circular cross section, and that is sized to secure a particular suction tube 11 or cable 12 therein. A second portion 25 of the opening 22 comprises a slot 22b that has a dimension that is smaller than the dimension of the first portion 22a. It is to be understood that while the embodiment shown in FIG. 2 illustrates an opening or grooves 22 for use with suction tubes 11 and cables 12, the sizing and number of openings or grooves 22 may be altered to meet particular requirement for different sized tubes 11 and cables 12. Consequently, the embodiment of the surgical attachment device 10a shown in FIG. 2 should not be taken as limiting.

The surgical attachment device 10a may have a length of about 1.57 inches, a width of about 1.95 inches, and a thickness of about 1.00 inches, for example. With respect to the opening or groove 22 shown in FIG. 2, it may be sized for use with the pneumatic tube 11, for example, and the first or circular portion 22a may have a diameter of about 0.56 inches, for example. This diameter is outwardly tapered from the center of the flexible member 21 toward each end. This permits removal of the member 21 from its mold. The width dimension of the slot 22b may be on the order of 0.36 inches in width, for example.

The opening 22 has a plurality of tapered ribs 27 that may be triangular, for example, disposed along the internal periphery of the opening 22 that taper from their widest dimension at respective ends of the opening 22 to their narrowest dimension adjacent the center of the opening 22. The plurality of tapered ribs 27 assist in securing the tube 11 or cable 12 in the groove 22 and prevent unwanted sliding and inadvertent thereof. The tapered ribs 27 have a diameter adjacent the respective ends of the opening 22 that is substantially equal to or narrower than the diameter of the opening 22 at its center (at the location where the tapered ribs 27 start to taper outward). A pair of projections 26 are present at the interface between the first and second portions 22a, 22b of the opening 22. The pair of projections 26 are larger than the other ribs 27 and serve to prevent inadvertent pull-out of the hose, cable tube or tube 12 from the opening 22. A surgical attachment device 10a that includes these projections 26 may be used to secure a pneumatic hose, for example.

An adhesive layer 28 is disposed on a second surface 29b of the member 21 so that it may be secured to the surgical drape 17 during an operation. The adhesive layer 28 may be comprised of any suitable adhesive, such as those commonly used in medical applications. The adhesive layer 28 is affixed or otherwise coated onto the second surface 29b of the flexible member 21 and a backing layer (not shown) such as is provided by wax-coated paper, for example, may be applied to the exposed surface of the adhesive layer 28. The backing layer is used to cover the adhesive layer 28 prior to use, and is peeled off to expose the adhesive layer 28, whereafter the surgical attachment device 10 is then secured to the drape 17.

Figure 4:
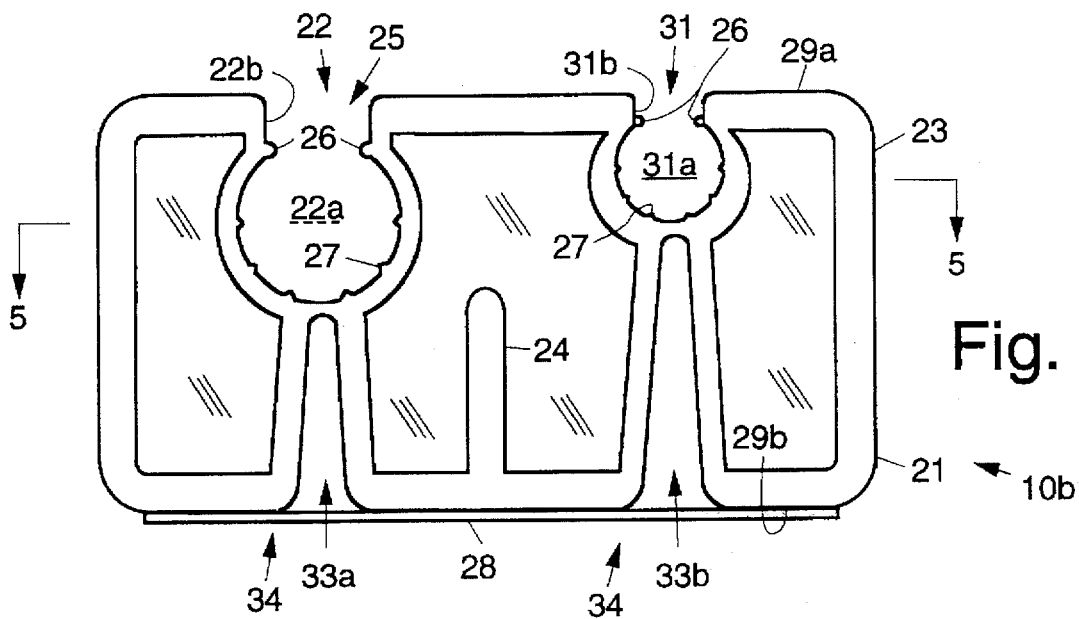
FIG. 4 is an end view of a second embodiment of the present surgical attachment device.
Figure 5:
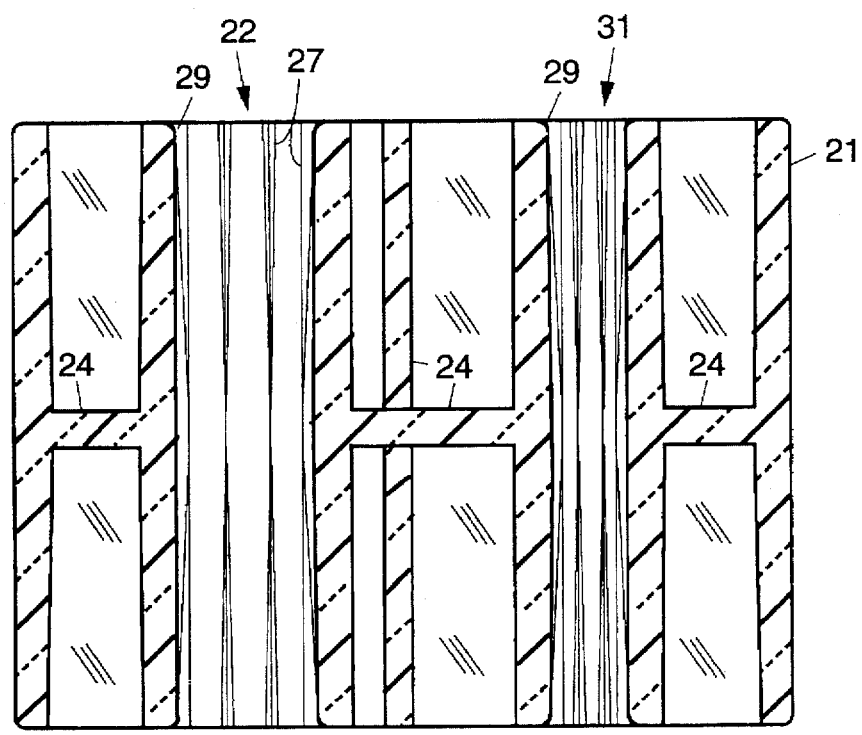
FIG. 5 is a cross sectional top view of the device of FIG. 4 taken along the lines 5—5.

Referring to FIG. 4, it is an end view of a second embodiment of the surgical attachment device 10b, while FIG. 5 is a cross sectional top view of the device 10b of FIG. 4 taken along the lines 5—5. In the surgical attachment device 10b shown in FIGS. 4 and 5, there are first and second openings 22, 31, and the first opening 22 is smaller than the opening 22 of the device 10b of FIG. 2. The diameter of a first portion 22a of the first opening 22 may be on the order of 0.34 inches, for example, and is designed to secure a fiber optic light source cable and video cable 12, for example. The slot 22b of the opening 22 is smaller than the diameter of the first portion 22a of the opening 22 and may be on the order of 0.29 inches, for example. The second opening 31 is formed in the member 21 and is sized for use with a video cable 12 and its first portion 31 a may have a diameter of about 0.18 inches, for example. A slot 31b of the second opening 31 may be on the order of 0.17 inches, for example.

In the second embodiment of the surgical attachment device 10b, the member 21 is flexible, and the first and second openings 22, 31 are made to open and close, by means of respective slots 33a, 33b that create two living hinges 34. The slots 33a, 33b separate two outer sections of the member 21 from a central section and are caused to flex by squeezing them toward the central section, thus opening the first and second openings 22, 31. The living hinges 34 return to their original positions after deformation of the openings 22, 31. Again, in the second embodiment of the surgical attachment device 10b, tubes 11 and cables 12, and the like, are secured in the first and second openings 22, 31 by the use of the ribs 27 that project into the respective openings 22, 31 and make contact with the respective tube 11 or cable 12.

Figure 6:
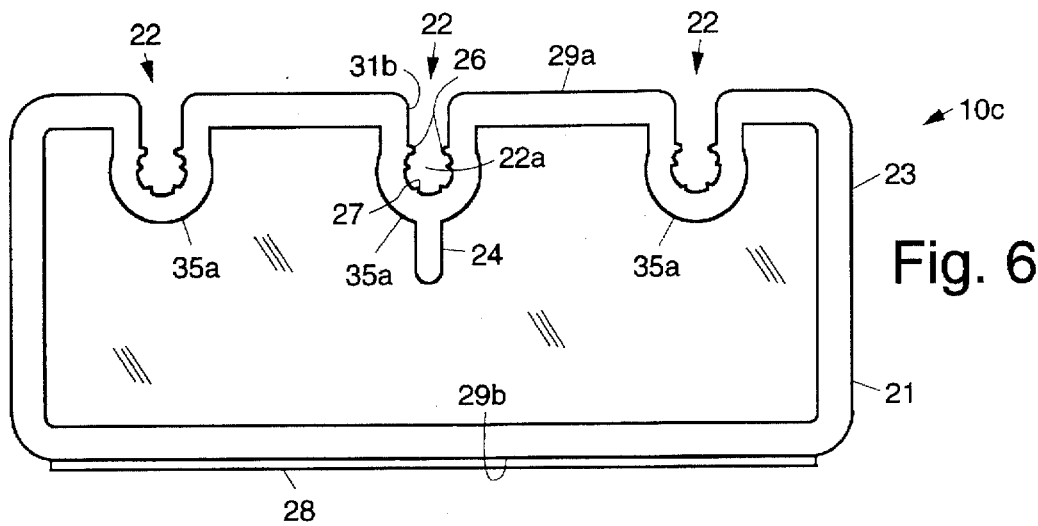
FIG. 6 shows a first end of a third embodiment of the present surgical attachment device.
Figure 7:
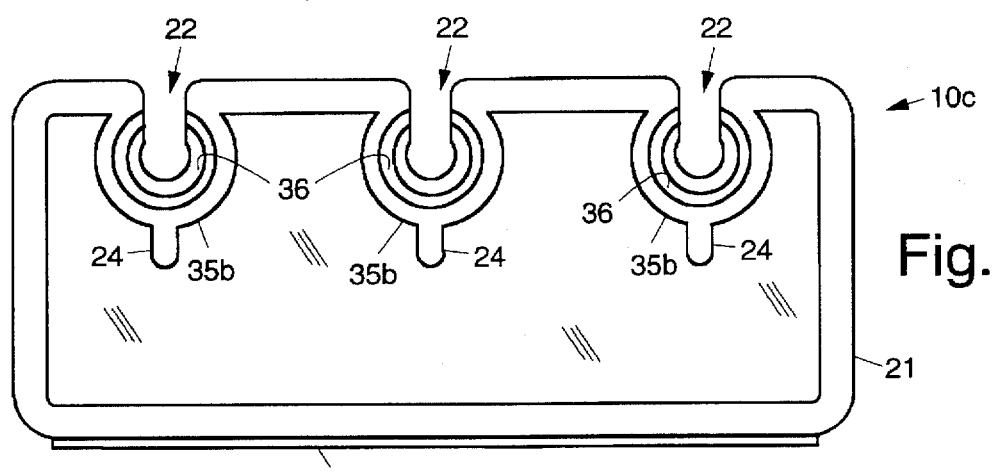
FIG. 7 shows a second end of the device of FIG. 6.
Figure 8:
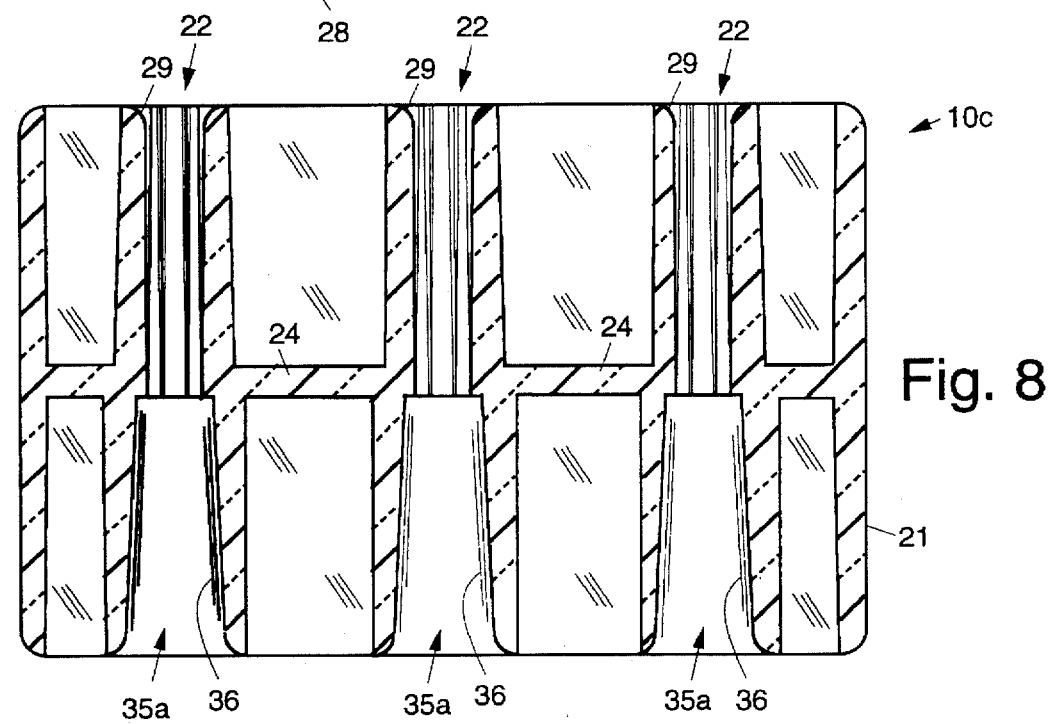
FIG. 8 is a cross sectional top view of the device of FIGS. 6 and 7 taken along the lines 8—8.

Referring to FIGS. 6 and 7, they show first and second ends of a third embodiment of the surgical attachment device 10c. FIG. 8 is a cross sectional top view of the device 10c of FIGS. 6 and 7 taken along the lines 8—8. The surgical attachment device 10c is designed to have three substantially configured openings 22. These openings 22 are designed to hold flexible intravenous (I-V) tubes 11 that is connected to a commonly-used in-line medication port (not shown) used to add medication to continuously running IV fluid, for example. Each opening 22 has a first portion 35a that includes the plurality of triangular ribs 27 that are used to secure the tubing. The most superficial ribs 27 (or projections 26) are larger than the rest of the ribs 27 and serve to restrict inadvertent pull-out of the tubing from the opening 22. A second portion 35b of the opening 22 is configured to mate with and secure the I-V port. The second portion 35b of the opening 22 has a taper 36 that tapers from the outer edge of the second portion 35b of the opening 22 toward the center of the member 21 and generally matches a tapered portion of the IV port.

Figure 9:
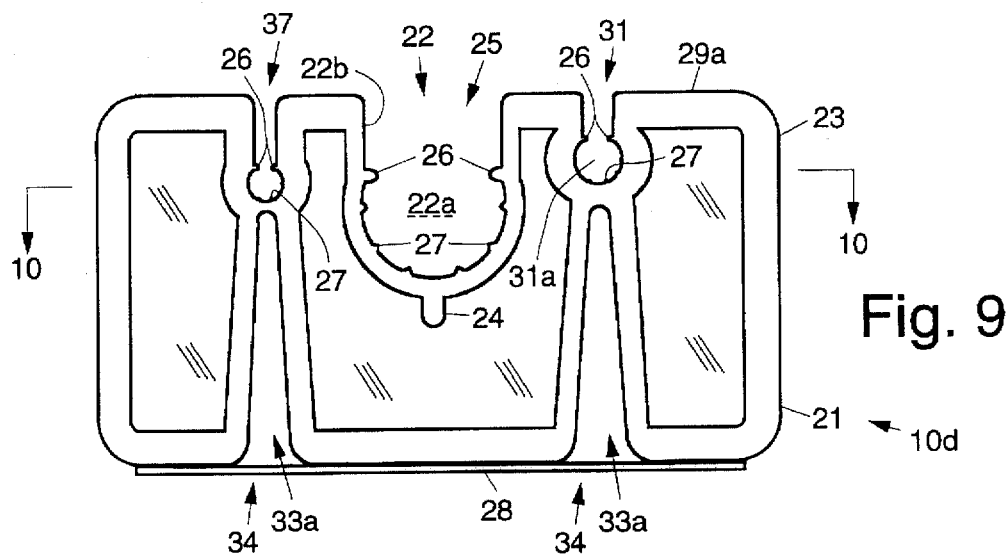
FIG. 9 is an end view of a fourth embodiment of the present surgical attachment device.
Figure 10:
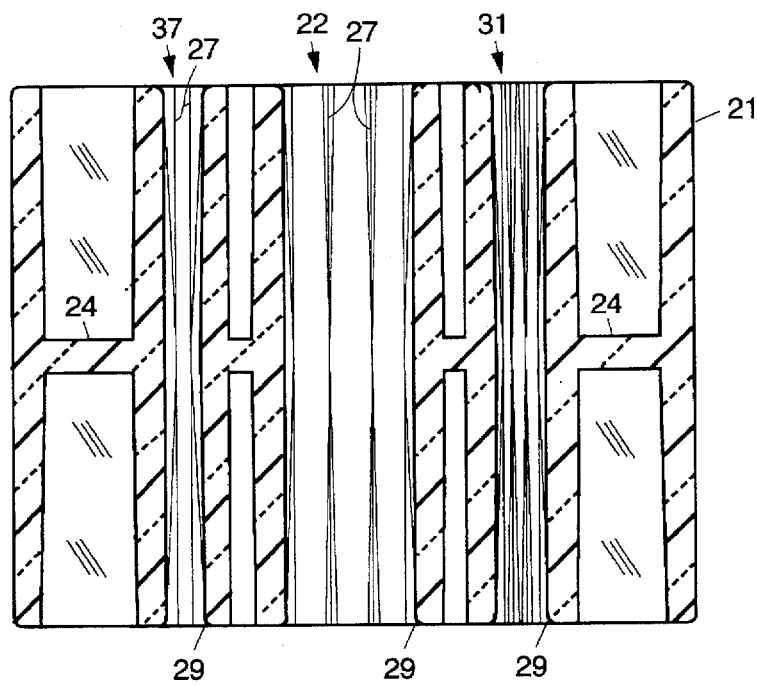
FIG. 10 is a cross sectional top view of the device of FIG. 9 taken along the lines 10—10.

Referring to FIGS. 9 and 10, they show end and cross sectional top views of a fourth embodiment of the surgical attachment device 10d. The fourth embodiment of the surgical attachment device 10d comprises three different sized openings 22, 31, 37. The second opening 31 is smaller than the first opening 22, and the third opening 37 is smaller than the second opening 31. The diameter of the first opening 22 may be on the order of 0.34 inches, for example, and is designed to secure suction tubing or cell saver suction tubing, for example. The diameter of the second opening 31 may be on the order of 0.12 inches, for example, and is designed to secure a unipolar electrical cable 12, for example. The diameter of the third opening 37 may be on the order of 0.07 inches, for example, and is designed to secure a bipolar electrical cable 12, for example. The discussion relating to FIGS. 2, 3, 4 and 5 describe the attributes of the structure of the fourth embodiment of the surgical attachment device 10d, and additional description is not believed to be necessary in understanding the invention.

The fourth embodiment of the surgical attachment device 10b includes living hinges 34, and the openings 31, 37 in are caused to flex by squeezing two outer sections of the member 21 toward a middle section thereof, thus opening the openings 31, 37. In the fourth embodiment of the surgical attachment device 10b, tubes 11 and cables 12, and the like, are secured in the three openings 22, 31, 37 by the use of the ribs 27 that project minimally into the respective openings 22, 31, 37 and make contact with the respective tube 11 or cable 12.

Due to generally coincident sizes of the openings 22, 31, 37 and ribs 27 and the cables 12, hose, or robe 11 passing through them, a certain amount of friction is produced. The length of the respective openings 22, 31, 37, in part, determines the friction or drag that is encountered by the tube 11 or cables 12 passing through them, when they are pulled or pushed through their respective openings 22, 31, 37. The length of the openings 22, 31, 37, the relative dimensions of the openings 22, 31, 37, and ribs 27, and the tube 11, hose, or cables 12 passing through them, are proportioned to provide optimal control of the tube 11 and cables 12. The ribs 27 are sufficient to prevent easy pull-out of the tubes 11 or cables 12, while easily allowing insertion of the tube 11 or cables 12 into their respective openings 22, 31, 37. The larger ribs 27 or projections 26 that are strategically placed, usually at the entrance to the opening 22a, prevent inadvertent pull-out of the tube hose, wires and cables.

Figure 11:
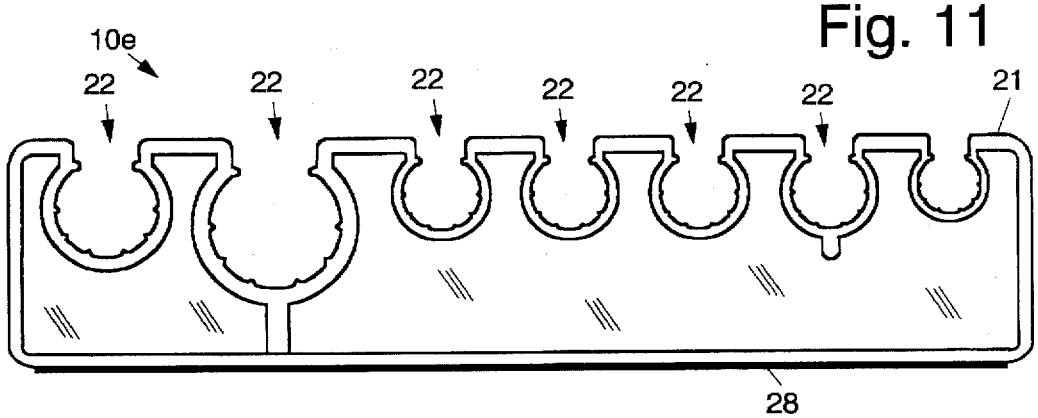
FIG. 11 is an end view of a fifth embodiment of the present surgical attachment device.

FIG. 11 is an end view of a fifth embodiment of the present surgical attachment device 10e. This embodiment of the device 10e is a cardiovascular manifold that secures multiple tubes 11 and cables 12 that are used in cardiovascular operations, and the like. Each of the openings 22 of the member 21 is designed as described above and secures a specific type of tube 11 or cable 12 therein.

It is to be understood that the number of openings 22 disclosed with reference to each of the embodiments of the device 10 may be only one opening 22 or may be a plurality of openings 22 as shown in the various disclosed embodiments. Furthermore, different variations of the disclosed embodiments may be constructed using the principles of the present invention to accommodate specific surgical situations.

In operation, in the embodiments of the surgical attachment device 10 having living hinges 34, the tubes 11 or cables 12 are inserted into the openings 22, 31, 37 by transiently deforming the narrower portion of each groove 22, 23, 24, deforming the tube 11, hose, or cable 12, or both, and pushing the tube 11, hose, or cable 12 into the openings 22, 31, 37. In the embodiments of the surgical attachment device 10 having openings without living hinges 34, the tubes 11 or cables 12 are inserted into the openings 22 by deforming the tube 11, hose, or cable 12, and pushing the tube 11, hose, or cable 12 into the openings 22.

Once the tube 11 or cable 12 is within its openings 22, 31, 37, the narrower portion of the openings 22, 31, 37 restricts unintended pull-out of the tube 11 or cables 12 from the attachment device 10. The length of the openings 22, 31, 37 and the dimensions of the tubes, cables, or hoses 11, 12 relative to their openings 22, 31, 37 and ribs 27 determines the drag coefficient as they are pulled therethrough. These proportions are designed to provide for intentional sliding through the openings 22, 31, 37, and also provide sufficient friction to resist most unwanted motion.

The surgical attachment devices 10 are preferably manufactured by molding the member 21 to form the openings 22, 31, 37 and living hinges 34. The adhesive layer 28 is then coated or disposed on the second surface 29b of the flexible member 21 and the backing layer is applied to the exposed surface of the adhesive layer 28. This assembly is then packaged and the packaged assembly is sterilized by means of gamma radiation sterilization procedures commonly used in the medical industry. During an operation, the sterilized package is opened, the surgical attachment devices 10 is removed from the package. The backing layer is removed from the surgical attachment devices 10 to expose the adhesive layer 28, and the surgical attachment device 10 is secured to the surgical drape 17, for example, in an appropriated place relative to the location of the surgery. The suction tube 11, hoses, and cables 12 are then inserted into the respective openings 22, 31, 37 to hold them in place during the surgery.

Thus there has been described a new and improved surgical attachment devices that may used to secure tubes, wires, hoses, electrical cables, video cables and fiber optic cables during an operation. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. Apparatus comprising:

a member having first and second surfaces and having an opening formed therein adjacent the first surface, wherein a first portion of the opening is dimensioned to slidably secure a cylindrically shaped member therein, and wherein the first portion of the opening tapers outwardly from a point adjacent a center of the member toward respective opposite ends of the opening, and wherein a second portion of the opening disposed immediately adjacent the first surface is dimensioned to be slightly smaller than the dimension of the first portion of the opening, and wherein the opening further comprises a plurality of inwardly projecting tapered ribs disposed around its internal periphery that taper from a narrowest dimension adjacent the center of the opening to a widest dimension at respective ends of each opening; and an adhesive layer disposed on the second surface of the flexible member.

2. The apparatus of claim 1 further comprising at least one projection disposed adjacent an interface between the first and second portions of the opening that projects inwardly relative to the opening.

3. The apparatus of claim 1 wherein the member is flexible.

4. The apparatus of claim 1 wherein the opening is dimensioned to secure a unipolar cable therein.

5. The apparatus of claim 1 wherein the opening is dimensioned to secure a bipolar cable therein.

6. The apparatus of claim 1 wherein the opening is dimensioned to secure an endoscopic cable therein.

7. The apparatus of claim 1 wherein the opening is dimensioned to secure a suction tube therein.

8. The apparatus of claim 1 wherein the opening is dimensioned to secure cardiovascular bypass tubing therein.

9. The apparatus of claim 1 wherein the opening is dimensioned to secure intravenous tubing therein.

10. The apparatus of claim 1 further comprising a plurality of openings formed adjacent the first surface of the flexible member that are respectively dimensioned to secure a plurality of cylindrically shaped members therein.

11. The apparatus of claim 10 wherein the plurality of openings are dimensioned to secure a suction tube and first and second cables therein, respectively.

12. The apparatus of claim 10 wherein the plurality of openings are dimensioned to secure a suction tube, a tripolar cable, and a bipolar cable therein, respectively.

13. A device for securing a tubular members to a surgical drape during an operation, said device comprising:

a flexible member having first and second surfaces and having an opening formed therein adjacent the first surface, wherein a first portion of the opening is dimensioned to slidably secure a predetermined tubular member therein, and wherein the first portion of the opening tapers outwardly from a point adjacent a center of the member toward respective opposite ends of the opening, and wherein the opening further comprises a plurality of inwardly projecting tapered ribs disposed around its internal periphery that taper from a narrowest dimension adjacent the center of the opening to a widest dimension at respective ends of each opening, and wherein a second portion of the opening disposed immediately adjacent the first surface is dimensioned to be slightly smaller than the dimension of the first portion of the opening, and wherein the flexible member is flexible adjacent the second portion of the opening to permit passage of the predetermined tubular member through the second portion of the opening and into the respective first portion of the opening to permit securing of the predetermined tubular member therein; and an adhesive layer disposed on the second surface for securing the flexible member to the surgical drape during an operation.

14. The device of claim 13 further comprising at least one projection disposed adjacent an interface between the first and second portions of the opening that projects inwardly relative to the opening.

15. The device of claim 13 wherein the predetermined tubular member comprises a unipolar cable.

16. The device of claim 15 wherein the predetermined tubular member comprises a bipolar cable.

17. The surgical attachment device of claim 13 wherein the predetermined tubular member comprises an endoscopic cable.

18. The surgical attachment device of claim 17 wherein the predetermined tubular member comprises a video cable.

19. The apparatus of claim 13 further comprising a plurality of openings formed adjacent the first surface of the flexible member that are respectively dimensioned to secure a plurality of tubular members therein.

20. The apparatus of claim 13 wherein the flexible member comprises a plurality of slots formed adjacent the second surface of the flexible member that are separated from selected openings by hinge areas.

21. Apparatus comprising:

a flexible member having first and second surfaces and having a plurality of openings formed therein adjacent the first surface, wherein first portions of the openings are dimensioned to slidably secure predetermined tubular members therein, and wherein the first portions of the openings taper outwardly from a point adjacent a center of the member toward respective opposite ends of the openings, and wherein the openings further comprise a plurality of inwardly projecting tapered ribs disposed around their internal peripheries that taper from a narrowest dimension adjacent the center of the openings to a widest dimension at respective ends of each openings, and wherein a second portion of the openings disposed immediately adjacent the first surface is dimensioned to be slightly smaller than the dimension of the first portion of the openings, and wherein the flexible member is flexible adjacent the second portion of the openings to permit passage of the predetermined tubular members through the second portion of the openings and into the respective first portion of the openings to permit securing of the predetermined tubular members therein, and wherein the openings further comprise a plurality of projections disposed adjacent an interface between the first and second portions of the openings that projects inwardly relative to the openings; and an adhesive layer disposed on the second surface of the flexible member.

22. The apparatus of claim 21 further comprising a plurality of lower slots formed adjacent the second surface of the flexible member that are separated from the respective first portions of the plurality of openings by a respective plurality of hinge areas.

23. The apparatus of claim 21 wherein the plurality of openings are dimensioned to secure selected tubular members consisting of suction tubes, wires, vacuum hoses, pneumatic hoses, electrical cables, video cables and fiber optic cables.

* * * * *